(12) United States Patent
Dean et al.

(10) Patent No.: US 7,375,105 B2
(45) Date of Patent: May 20, 2008

(54) PYRIDINE SUBSTITUTED FURAN DERIVATIVES AS RAF KINASE INHIBITORS

(75) Inventors: David Kenneth Dean, Harlow (GB); Andrew Kenneth Takle, Harlow (GB); David Matthew Wilson, Harlow (GB)

(73) Assignee: SmithKline Beecham p.l.c., Brentford, Middlesex (GB)

( * ) Notice: Subject to any disclaimer, the term of this patent is extended or adjusted under 35 U.S.C. 154(b) by 458 days.

(21) Appl. No.: 10/488,650

(22) PCT Filed: Sep. 5, 2002

(86) PCT No.: PCT/EP02/09944

§ 371 (c)(1),
(2), (4) Date: Mar. 4, 2004

(87) PCT Pub. No.: WO03/022838

PCT Pub. Date: Mar. 20, 2003

(65) Prior Publication Data

US 2004/0248896 A1 Dec. 9, 2004

(30) Foreign Application Priority Data

Sep. 5, 2001 (GB) ................. 0121485.7
Sep. 5, 2001 (GB) ................. 0121493.1

(51) Int. Cl.
*A61K 31/5377* (2006.01)
*A61K 31/4545* (2006.01)
*A61K 31/443* (2006.01)
*C07D 413/14* (2006.01)
*C07D 211/32* (2006.01)
*C07D 405/04* (2006.01)

(52) U.S. Cl. .................. 514/231.5; 514/318; 514/326; 544/152; 546/194; 546/283.4

(58) Field of Classification Search .............. 546/194, 546/283.4; 544/152; 514/231.5, 318, 326
See application file for complete search history.

(56) References Cited

U.S. PATENT DOCUMENTS

| 4,735,958 A | 4/1988 | Roth et al. |
| 5,776,954 A | 7/1998 | De Laszlo et al. |
| 5,792,778 A | 8/1998 | De Laszlo et al. |

FOREIGN PATENT DOCUMENTS

| WO | WO 99/32455 | 7/1999 |
| WO | WO 01/34149 | 5/2001 |
| WO | WO 01/34150 | 5/2001 |
| WO | WO 01/38324 | 5/2001 |
| WO | WO 01/87877 | 11/2001 |

OTHER PUBLICATIONS

Wermuth, C.G. (ed.), "Chapter 13: Molecular Variations Based on Isosteric Replacements", *The Practice of Medicinal Chemistry*, pp. 204-237, Academic Press Ltd., Copyright (1996), XP-002190259.

*Primary Examiner*—Bernard Dentz
(74) *Attorney, Agent, or Firm*—Grace C. Hsu; Mary E. McCarthy; Charles M. Kinzig

(57) ABSTRACT

Compounds and their use as pharmaceuticals particularly as Raf kinase inhibitors for the treatment of neurotraumatic diseases, cancer, chronic neurodegeneration, pain, migraine and cardiac hypertrophy. Wherein X is O, $CH_2$ CO, S or NH, or the moiety $X-R^1$ is hydrogen; $Y_1$ and $Y_2$ independently represent CH or N; Ar is a mono- or fused bicyclic aromatic or heteroaromatic group which may be optionally substituted; one of $X_1$ and $X_2$ is selected from O, S or $NR^{11}$ and the other is CH, wherein $R^{11}$ is hydrogen, $C_{1-6}$alkyl, aryl or aryl$C_{1-6}$alkyl.

6 Claims, No Drawings

PYRIDINE SUBSTITUTED FURAN DERIVATIVES AS RAF KINASE INHIBITORS

This application is a §371 national stage filing of PCT/EP02/09944 filed 5 Sep. 2002.

This invention relates to novel compounds and their use as pharmaceuticals, particularly as Raf kinase inhibitors for the treatment of neurotraumatic diseases, cancer, chronic neurodegeneration, pain, migraine and cardiac hypertrophy.

Raf protein kinases are key components of signal transduction pathways by which specific extracellular stimuli elicit precise cellular responses in mammalian cells. Activated cell surface receptors activate ras/rap proteins at the inner aspect of the plasma-membrane which in turn recruit and activate Raf proteins. Activated Raf proteins phosphorylate and activate the intracellular protein kinases MEK1 and MEK2. In turn, activated MEKs catalyse phosphorylation and activation of p42/p44 mitogen-activated protein kinase (MAPK). A variety of cytoplasmic and nuclear substrates of activated MAPK are known which directly or indirectly contribute to the cellular response to environmental change. Three distinct genes have been identified in mammals that encode Raf proteins; A-Raf, B-Raf and C-Raf (also known as Raf-1) and isoformic variants that result from differential splicing of mRNA are known.

Inhibitors of Raf kinases have been suggested for use in disruption of tumor cell growth and hence in the treatment of cancers, e.g. histiocytic lymphoma, lung adenocarcinoma, small cell lung cancer and pancreatic and breast carcinoma; also in the treatment and/or prophylaxis of disorders associated with neuronal degeneration resulting from ischemic events, including cerebral ischemia after cardiac arrest, stroke and multi-infarct dementia and also after cerebral ischemic events such as those resulting from head injury, surgery and/or during childbirth; also in chronic neurodegeneration such as Alzheimer's disease and Parkinson's disease; also in the treatment of pain, migraine and cardiac hypertrophy.

We have now found a group of novel compounds that are inhibitors of Raf kinases, in particular inhibitors of B-Raf kinase. We have also found a group of compounds which have activity against B-Raf kinase.

According to the invention there is provided the use of compounds of formula (I):

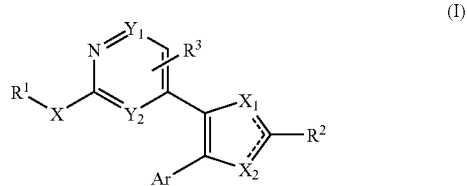

wherein

X is O, $CH_2$, CO, S or NH, or the moiety X—$R^1$ is hydrogen;

$Y_1$ and $Y_2$ independently represent CH or N;

$R^1$ is hydrogen, $C_{1-6}$alkyl, $C_{3-7}$cycloalkyl, aryl, aryl $C_{1-6}$alkyl-, heterocyclyl, heterocyclyl$C_{1-6}$alkyl-, heteroaryl, or heteroaryl$C_{1-6}$alkyl-, any of which, except hydrogen, may be optionally substituted;

$R^2$ is $C_{1-6}$ alkyl, $C_{3-7}$cycloalkyl, heterocyclyl, heterocyclyl$C_{1-6}$alkyl, hetero$C_{1-6}$alkyl, or $C_{1-6}$alkylhetero$C_{1-6}$alkyl, any one of which may be optionally substituted;

Ar is a mono- or fused bicyclic aromatic or heteroaromatic group which may be optionally substituted;

$R^3$ is independently selected from hydrogen, halogen, $C_{1-6}$alkyl, aryl, aryl$C_{1-6}$alkyl, $C_{1-6}$alkoxy, $C_{1-6}$alkoxy $C_{1-6}$alkyl, halo$C_{1-6}$alkyl, aryl$C_{1-6}$alkoxy, hydroxy, nitro, cyano, azido, amino, mono- and di-N—$C_{1-6}$alkylamino, acylamino, arylcarbonylamino, acyloxy, carboxy, carboxy salts, carboxy esters, carbamoyl, mono- and di-N—$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl or $C_{1-6}$alkylsulphonyl; and one of $X_1$ and $X_2$ is selected from O, S or $NR^{11}$ and the other is CH, wherein $R^{11}$ is hydrogen, $C_{1-6}$alkyl, aryl or aryl$C_{1-6}$alkyl;

or pharmaceutically acceptable salts thereof as inhibitors of B-Raf kinase.

Compounds wherein $X_2$ is N, X—$R^1$=H, $Y_1$=$Y_2$=CH, $R^3$ is H, Ar is 4-fluorophenyl and $R^2$ is methyl, NMe-piperidine or c-hexane are disclosed in Bioorg. Med. Chem. Lett; (1999), 9, 641-646 as ligands of the human glucagon receptor and inhibitors of p38 kinase.

Certain pyrrole compounds are disclosed in U.S. Pat. No. 5,776,954 (WO97/16442) as glucagon antagonists and inhibitors of TNF and IL1 biosynthesis and action useful in as agents for the treatment of diabetes or other cytokine mediated disease.

Certain pyrrole compounds are disclosed in U.S. Pat. No. 5,792,778 (WO97/05877) as inhibitors of TNF-α and IL-1, IL-6 mediated diseases. e.g. diabetes. Compounds wherein $X_2$ is N, X—$R^1$ is H, $R^3$ is H, $Y_1$=$Y_2$=CH, Ar is 4-fluorophenyl and $R^2$ is methyl, t-butyl, 4-(N-substituted)-piperidine, $CH_2$-4(N-Me)-piperazine, $CH_2$—N-morpholine, 3-N-Me-piperidine, cyclohexyl, isopropyl or 1-cyclopropylethyl are disclosed as treatments for cytokine-mediated disease in WO97/16426. Compounds wherein $R_2$ is 4-(N-substituted) piperidine and $X_2$ is NH, X—$R^1$ is H, $R^3$ is H, $Y_1$=$Y_2$=CH, Ar is 4-fluorophenyl are disclosed as antiprotozoal agents in WO01/34632, WO01/34150 and WO01/34149.

As a further aspect of the invention there is provided compounds of formula (Ia):

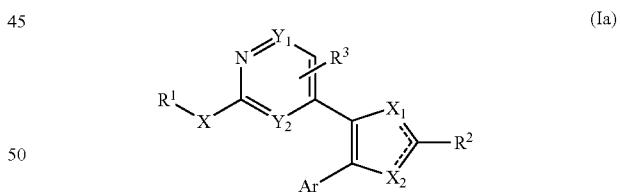

wherein

X is O, $CH_2$, CO, S or NH, or the moiety X—$R^1$ is hydrogen;

$Y_1$ and $Y_2$ independently represent CH or N;

$R^1$ is hydrogen, $C_{1-6}$alkyl, $C_{3-7}$cycloalkyl, aryl, aryl $C_{1-6}$alkyl-, heterocyclyl, heterocyclyl$C_{1-6}$alkyl-, heteroaryl, or heteroaryl$C_{1-6}$alkyl-, any of which, except hydrogen, may be optionally substituted;

$R^2$ is $C_{1-6}$alkyl, $C_{3-7}$cycloalkyl, heterocyclyl, heterocyclyl$C_{1-6}$alkyl, hetero$C_{1-6}$alkyl, or $C_{1-6}$alkylhetero$C_{1-6}$alkyl, any one of which may be optionally substituted;

Ar is a mono- or fused bicyclic aromatic or heteroaromatic group which may be optionally substituted;

$R^3$ is independently selected from hydrogen, halogen, $C_{1-6}$alkyl, aryl, aryl$C_{1-6}$alkyl, $C_{1-6}$alkoxy, $C_{1-6}$alkoxy $C_{1-6}$alkyl, halo$C_{1-6}$alkyl, aryl$C_{1-6}$alkoxy, hydroxy, nitro, cyano, azido, amino, mono- and di-N—$C_{1-6}$alkylamino, acylamino, arylcarbonylamino, acyloxy, carboxy, carboxy salts, carboxy esters, carbamoyl, mono- and di-N—$C_{1-6}$alkylcarbamoyl, $C_{1-4}$alkoxycarbonyl, aryloxycarbonyl, ureido, guanidino, $C_{1-4}$alkylguanidino, amidino, $C_{1-6}$alkylamidino, sulphonylamino, aminosulphonyl, $C_{1-6}$alkylthio, $C_{1-6}$alkylsulphinyl or $C_{1-6}$alkylsulphonyl; and one of $X_1$ and $X_2$ is selected from O, S or $NR^{11}$ and the other is CH, wherein $R^{11}$ is hydrogen, $C_{1-6}$alkyl, aryl or aryl$C_{1-6}$alkyl;

with the proviso that when $X_2$ is N, X—$R^1$=H, $Y_1$=$Y_2$=CH, and provided that the compounds are not Example 47 or the step 3 intermediate of Example 47, Examples 48, 145-148, 176, 177, 186-195 of U.S. Pat. No. 5,776,964; or Examples 1-42, 106, 107, Example 116 and compounds of Step 4 and 6 Example 116, Example 117, Example 118 and intermediates, Example 119-126, compound step 1 of Example 127, Examples 128 and 129, step 3 Example 129, and Examples 131-133 of U.S. Pat. No. 5,792,778;

or pharmaceutically acceptable salts thereof.

As used herein, the double bond indicated by the dotted lines of formula (I), represents the possible regioisomeric ring forms of the compounds falling within the scope of this invention, the double bond being between the non-heteroatoms.

Alkyl and alkenyl groups referred to herein, individually or as part of larger groups e.g. alkoxy, may be straight or branched groups containing up to six carbon atoms and are optionally substituted by one or more groups selected from the group consisting of aryl, heteroaryl, heterocyclyl, $C_{1-6}$alkoxy, $C_{1-6}$-alkylthio, aryl$C_{1-6}$alkoxy, aryl$C_{1-6}$alkylthio, amino, mono- or di-$C_{1-6}$alkylamino, cycloalkyl, cycloalkenyl, carboxy and esters thereof, amide, sulphonamido, ureido, guanidino, $C_{1-4}$alkylguanidino, amidino, $C_{1-6}$alkylamidino, $C_{1-6}$acyloxy, azido, hydroxy, hydroxyimino and halogen.

Cycloalkyl and cycloalkenyl groups referred to herein include groups having from three to seven ring carbon atoms and are optionally substituted as described hereinabove for alkyl and alkenyl groups.

When used herein hetero$C_{1-4}$alkyl- means a $C_{1-6}$ carbon chain wherein the end carbon atom in the chain is substituted by a heteroatom selected from N, O, or S for example $C_{1-6}$alkylamino, $C_{1-6}$alkyloxy or $C_{1-4}$alkylthio.

$C_{1-6}$alkylhetero$C_{1-6}$alkyl means a $C_{3-13}$alkyl chain wherein one of the carbon atoms has been replaced with a heteroatom selected from N, O, or S, for example $C_{1-6}$alkylamino$C_{1-6}$alkyl or $C_{1-6}$ alkylaminodi$C_{1-6}$alkyl, $C_{1-6}$alkyloxy$C_{1-6}$alkyl-, $C_{1-6}$alkylthio$C_{1-6}$alkyl-, or $C_{1-4}$ alkylthiodi$C_{1-6}$alkyl.

When used herein, the term "aryl" includes, unless otherwise defined, single and fused rings suitably containing from 4 to 7, preferably 5 or 6, ring atoms in each ring, which rings, may each be unsubstituted or substituted by, for example, up to three substituents.

Suitable aryl groups include phenyl and naphthyl such as 1-naphthyl or 2-naphthyl.

Optional substituents for alkyl, alkenyl, cycloalkyl and cycloalkenyl groups include aryl, heteroaryl, heterocyclyl, $C_{1-6}$alkoxy, $C_{1-6}$alkylthio, aryl$C_{1-6}$alkoxy, aryl$C_{1-6}$alkylthio, amino, mono- or di-$C_{1-6}$alkylamino, aminosulphonyl, cycloalkyl, cycloalkenyl, carboxy and esters thereof, amide, ureido, quanidino, $C_{1-6}$alkylquanidino, amidino, $C_{1-6}$alkylamidino, $C_{1-6}$acyloxy, hydroxy, cyano and halogen or any combination thereof. Preferably the substituents are mono- or di-$C_{1-6}$alkylamino, heterocyclo$C_{3-6}$alkylamino, or $C_{2-6}$acylamino.

Alternatively the optional substituent contains a water-solubilising group; suitable solubilising moieties will be apparent to those skilled in the art and include hydroxy and amine groups. Even more preferably the optional substituent includes amino, mono- or di-$C_{1-6}$alkylamino, amine containing heterocyclyl, or hydroxy or any combination thereof.

When used herein the term "mono-cyclic" means an aromatic or heteroaromatic group having a 3 to 8 membered ring system for example phenyl, pyridine or pyran.

When used herein the term "bicyclic ring" means an aromatic or heteroaromatic fused ring system in which at least one of the rings is aromatic or heteroaromatic for example naphthyl, indole, benzofuran, indene, fused phenylcyclohexane, or fused phenyl cyclopentane.

When used herein the term "heterocyclyl" includes, unless otherwise defined, non-aromatic, single or fused, saturated or unsaturated rings, suitably containing up to four heteroatoms in each ring, each of which is selected from O, N and S, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring. Examples of heterocyclyl groups include pyrrolidine, piperidine, piperazine, morpholine, thiomorpholine, imidazolidine and pyrazolidine wherein any one of the groups piperidine, piperazine, morpholine and thiomorpholine can have at least one double bond.

When used herein, the term "heteroaryl" includes, unless otherwise defined, mono- and bicyclic heteroaromatic ring systems comprising up to four, preferably 1 or 2, heteroatoms each selected from O, N and S. Each ring may have from 4 to 7, preferably 5 or 6, ring atoms. A bicyclic heteroaromatic ring system may include a carbocyclic ring. Examples of heteroaryl groups include pyrrole, quinoline, isoquinoline, pyridine, pyrimidine, oxazole, thiazole, thiadiazole, triazole, imidazole and benzimidazole.

Aryl, heterocyclyl, heteroaryl, mono and bicyclic groups may be optionally substituted by preferably up to three substituents. Suitable substituents include halogen, hydroxy, $C_{1-6}$alkyl, aryl, aryl $C_{1-6}$alkyl, $C_{1-6}$alkoxy, $C_{1-6}$alkoxy $C_{1-6}$alkyl, halo $C_{1-6}$alkyl, aryl$C_{1-4}$alkoxy, hydroxy, nitro, cyano, azido, amino, mono- and di-N—$C_{1-6}$alkylamino, acylamino, arylcarbonylamino, acyloxy, carboxy, carboxy salts, carboxy esters, carbamoyl, mono- and di-N—$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-4}$alkylthio, $C_{1-6}$alkylsulphinyl, $C_{1-6}$alkylsulphonyl, heterocyclyl, heteroaryl, heterocyclyl $C_{1-6}$alkyl, hydroxyimino-$C_{1-6}$alkyl and heteroaryl $C_{1-4}$alkyl, and combinations thereof.

Preferably the optional substituent contains a water-solubilising group; suitable solubilising moieties will be apparent to those skilled in the art and include hydroxy and amine groups. Even more preferably the optional substituent includes amino, mono- or di-$C_{1-6}$alkylamino, amine containing heterocyclyl, or hydroxy or any combination thereof.

When used herein the term halo represents fluoro, chloro, bromo or iodo.

X is preferably NH or X—$R^1$ is preferably hydrogen.

When X is NH, $R^1$ is preferably hydrogen or $C_{1-6}$alkyl.

When $Y_1$ and $Y_2$ are CH, X—$R^1$ is preferably hydrogen.

When $Y_2$ is N, $R^1$ is preferably H or $C_{1-6}$alkyl.

Preferably $R^{11}$ is hydrogen.

Most preferably $X—R^1$ is hydrogen

Preferably $X_1$ or $X_2$ is O or S, more preferably O.

Preferably Ar is an optionally substituted phenyl, most preferably phenol.

Preferably $R^2$ is an optionally substituted $C_{1-6}$alkyl.

Preferably the substituents on $R^2$ are amino or substituted amino. Preferred substituents for the group Ar include halo, hydroxy, hydroxy $C_{1-6}$alkyl, hydroxyimino-$C_{1-6}$alkyl and $C_{1-6}$alkoxy.

Most preferably the compounds of the invention are of formula (II);

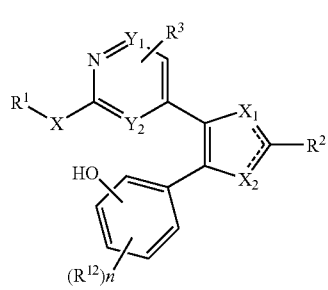

(II)

wherein $R^1$, X, $Y_1$, $Y_2$, $R^3$, $X_1$, $X_2$ and $R^2$ are as described for compounds of formula (I); each $R^{12}$ is independently selected from halo, hydroxy, $C_{1-4}$alkyl, $C_{1-4}$alkoxy; and n is 0, 1 or 2; or pharmaceutically acceptable salts thereof.

Preferably $R^{12}$ is halo, more preferably chlorine.

Preferably n is 1.

The compounds of formula (I) preferably have a molecular weight of less than 800

It will be understood that the invention includes pharmaceutically acceptable derivatives of compounds of formula (I) and that these are included within the scope of the invention.

Particular compounds according to the invention include those mentioned in the examples and their pharmaceutically acceptable salts. As used herein "pharmaceutically acceptable derivatives" includes any pharmaceutically acceptable salt, ester or salt of such ester of a compound of formula (I) which, upon administration to the recipient, is capable of providing (directly or indirectly) a compound of formula (I) or an active metabolite or residue thereof.

It will be appreciated that for use in medicine the salts of the compounds of formula (I) should be pharmaceutically acceptable. Suitable pharmaceutically acceptable salts will be apparent to those skilled in the art and include those described in *J. Pharm. Sci.*, 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amounts of water.

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Compounds of formula (I) are furan, pyrrole and thiophene derivatives which may be readily prepared, using procedures well-known to those skilled in the art, from starting materials which are either commercially available or can be prepared from such by analogy with well-known processes. For instance see, W. Friedrichsen (p351, furans), R. J. Sundberg (p 119, pyrroles) and J. Nakayama (p 607, thiophenes) in *Comprehensive Heterocyclic Chemistry II*, volume 2, series eds. A. R. Katritzky, C. W. Rees and E. F. V. Scriven, Typically, compounds of this invention may be prepared by a Paal-Knorr synthesis from a 1,4-dicarbonyl precursor, as outlined in Scheme 1 (where the groups $R_1X$, and $R^3$ are hydrogen, and $Y_1$ and $Y_2$ are CH). For example, base (e.g. diethylamine) mediated condensation of a methyl-ketone derivative with pyridine-4-carboxaldehyde results in the formation of a chalcone derivative (1, see S. E. deLaszlo et al *Bioorg. Med. Chem. Lett.*, 1999, 9, 641). Subsequent reaction of the chalcone (1) with an aryl carboxaldehyde and catalytic sodium cyanide under Stetter conditions (H. Stetter and K. Kuhlmann, *Org. React.*, 1991, 40, 407) generates the aforementioned 1,4-dicarbonyl precursor (2). Cyclisation under the appropriate conditions then results in the formation of the desired furan (e.g. phosphorus pentoxide-methanesulphonic acid or concentrated sulphuric acid or HCl/acetone/dioxan), pyrrole (e.g. ammonium acetate, acetic acid) or thiophene (e.g. Lawessons reagent) ring systems (3). Thereafter, the group $R^2$ may be converted into another group $R^2$, using conventional functional group. It will also be appreciated to one skilled in the art, that the aldehyde components could be utilised in reverse order generating the chalcone derivative (4) and subsequently the regioisomeric heterocycles (5).

Scheme 1

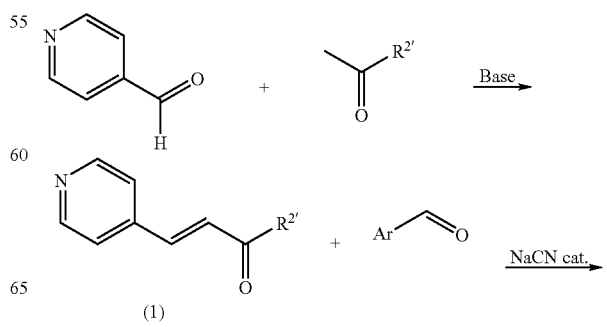

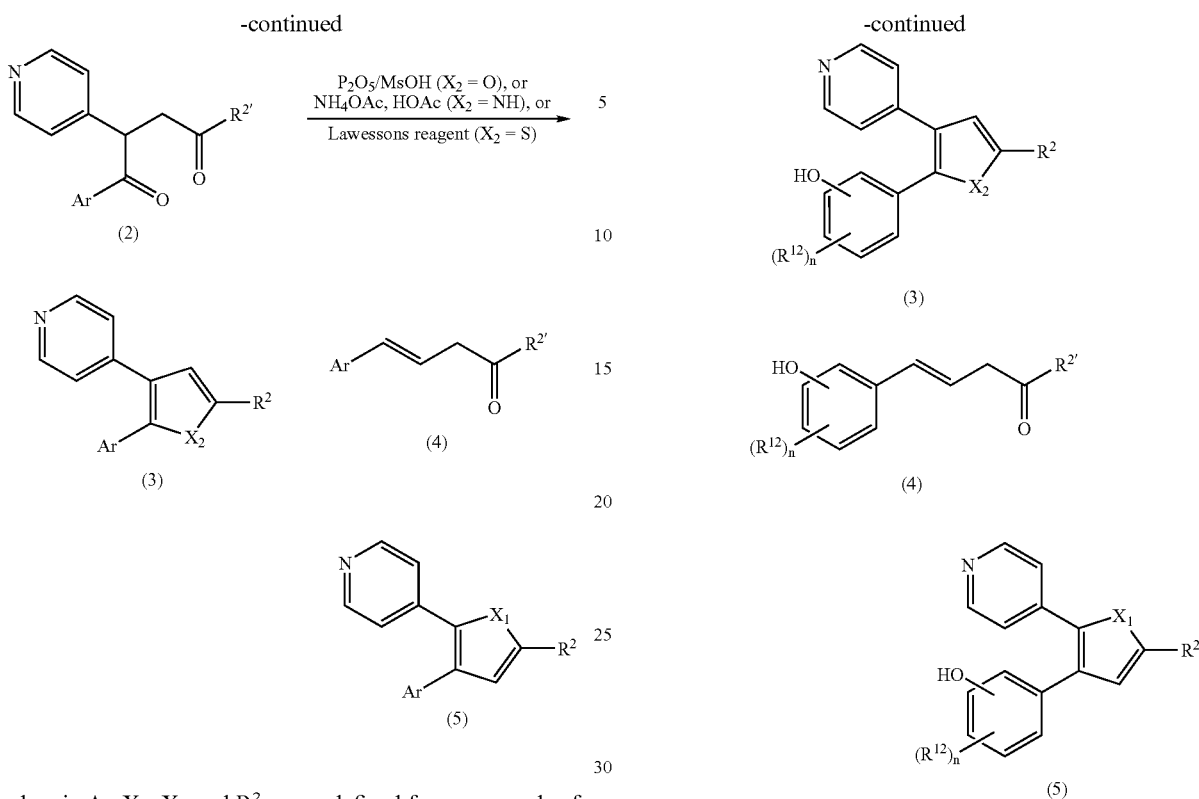

wherein Ar, $X_1$, $X_2$ and $R^2$ are as defined for compounds of formula (I).

Compounds of formula (II) can also be prepared as set out in scheme 2.

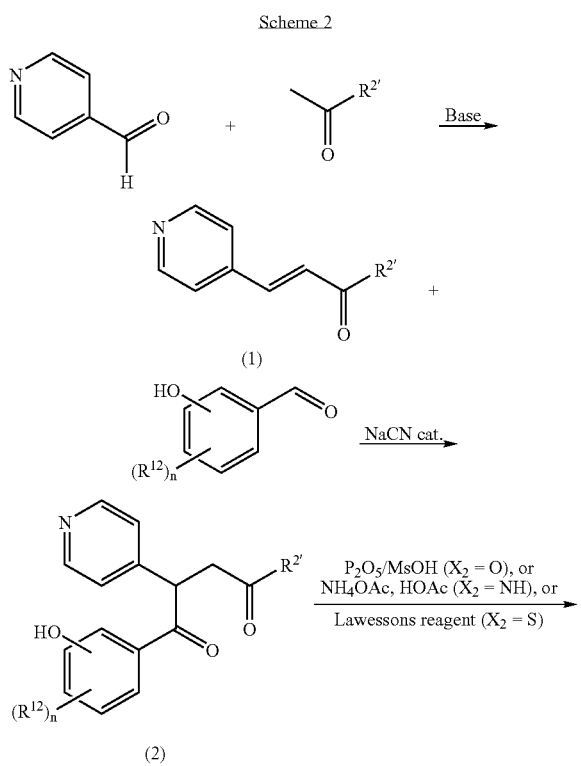

wherein $R^{12}$, n, $X_1$, $X_2$ and $R^2$ are as defined for compounds of formula (II).

During the synthesis of the compounds of formula (I) labile functional groups in the intermediate compounds, e.g. hydroxy, carboxy and amino groups, may be protected. A comprehensive discussion of the ways in which various labile functional groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Pharmaceutically acceptable salts may be prepared conventionally by reaction with the appropriate acid or acid derivative.

The novel carboxylic esters and the corresponding acids and aldehydes of formula (III) and (IV) which are used as intermediates in the synthesis of the compounds of formula (I) and (II) also form part of the present invention:

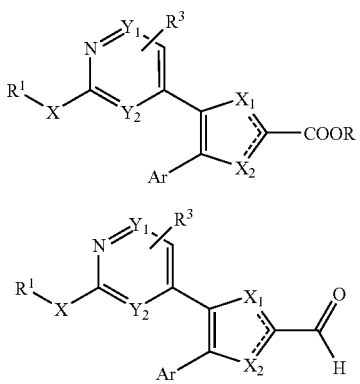

wherein X, $Y_1$, $Y_2$, $R^1$, $R^3$, Ar, $X_1$ and $X_2$ are as defined for compounds of formula (I) and R is hydrogen, $C_{1-6}$alkyl or aryl$C_{1-6}$alkyl.

As indicated above the compounds of formula (I) and their pharmaceutically acceptable derivatives are useful for the treatment and/or prophylaxis of disorders in which Raf kinases, in particular B-Raf kinase, are implicated.

According to a further aspect of the invention there is provided the use of a compound of formula (I) or a pharmaceutically acceptable salt thereof as an inhibitor of B-Raf kinase.

As indicated above the compounds of formula (I) and their pharmaceutically acceptable derivatives are useful in the treatment and/or prophylaxis of disorders associated with neuronal degeneration resulting from ischemic events, as well as chronic neurodegeneration, pain, migraine and cardiac hypertrophy.

As indicated above the compounds of formula (I) and their pharmaceutically acceptable derivatives are useful in the treatment and/or prophylaxis of disorders associated with neuronal degeneration resulting from ischemic events.

According to a further aspect of the invention there is provided a method of treatment or prophylaxis of a neurotraumatic disease, in a mammal in need thereof, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of any disease state in a human, or other mammal, which is exacerbated or caused by a neurotraumatic event.

Neurotraumatic diseases/events as defined herein include both open or penetrating head trauma, such as caused by surgery, or a closed head trauma injury, such as caused by an injury to the head region. Also included within this definition is ischemic stroke, particularly to the brain area, transient ischemic attacks following coronary by-pass and cognitive decline following other transient ischemic conditions.

Ischemic stroke may be defined as a focal neurologic disorder that results from insufficient blood supply to a particular brain area, usually as a consequence of an embolus, thrombi, or local atheromatous closure of the blood vessel. Roles for stress stimuli (such as anoxia), redox injury, excessive neuronal excitatory stimulation and inflammatory cytokines in this area has been emerging and the present invention provides a means for the potential treatment of these injuries. Relatively little treatment, for an acute injury such as these has been available.

The compounds of the invention may also be used in the treatment or prophylaxis of cancers. It is suggested that the compounds are effective in tumors that have activating B-Raf mutations (V599E) as well as tumors that are activated by Ras mutation. Mutations may occur in the Ras family members such as Kras2 with mutation G13D. Furthermore compounds of the invention may be used in the treatment or prophylaxis of colorectal cancer and melanoma According to a further aspect of the invention there is provided a method of treatment or prophylaxis of a patient suffering from or susceptible to cancer which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of cancer.

The compounds of formula (I) and pharmaceutically acceptable derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as combination with surgical therapy and radiotherapy. Combination therapies according to the present invention thus comprise the administration of at least one compound of formula (I) or a pharmaceutically acceptable derivative thereof, and the use of at least one other cancer treatment method. Preferably, combination therapies according to the present invention comprise the administration of at least one compound of formula (I) or a pharmaceutically acceptable derivative thereof, and at least one other pharmaceutically active chemotherapeutic agent. These include existing and prospective chemotherapeutic agents. The compound(s) of formula (I) and the other pharmaceutically active chemotherapeutic agent(s) may be administered together in a unitary pharmaceutical composition or separately and, when administered separately this may occur simultaneously or sequentially in any order. Such sequential administration may be close in time or remote in time. The amounts of the compound(s) of formula (I) and the other pharmaceutically active chemotherapeutic agent(s) and the relative timings of administration will be selected in order to achieve the desired combined therapeutic effect.

Pharmaceutically active chemotherapeutic agents which can be useful in combination with a compound of formula (I) or a pharmaceutically acceptable derivative thereof, include but are not restricted to the following:

(1) cell cycle specific anti-neoplastic agents include, but are not limited to, diterpenoids such as paclitaxel and its analog docetaxel; tubulin poisons such as taxol/taxane or vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludarabine, methotrexate, cladrabine, cytarabine, mercaptopurine, gemcitabine, and thioguanine; and camptothecins such as 9-amino camptothecin, irinotecan, topotecan, and the various optical forms of 7-4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, dacarbazine and nitrosoureas; anti-tumour antibiotics such as doxorubicin, daunomycin, epirubicin, idarubicin, mitomycin-C, dactinomycin, bleomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progestrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestrogens; mitoxantrone, 1-asparaginase, urokinase plasminogen activator receptor function inhibitors; inhibitors or c-kit and bcr/abl tyrosine kinases, (such as Gleevec), immunotherapy, immunoconjugates, cytokines (such as IL-2, IFN alpha and beta), tumor vaccines (including dendritic cell vaccines), thalidomide, COX-2 inhibitors, glucocorticoids (such as prednisone and decadron), radiation sensitizers, (such as temazolamide), growth factor function inhibitors such as inhibitors of the functions of hepatocyte growth factor; erb-B2, erb-B4, epidermal growth factor receptor (EGFR) and platelet derived growth factor receptors (PDGFR); inhibitors of angiogenesis such as inhibitors of the function of Ephrin receptors (such as, EphB4), vascular endothelial growth factor receptors (VEGFR) and the angiopoietin receptors (Tie1 and Tie2); and other kinase inhibitors such as inhibitors of CDK2 and CDK4.

Anti-neoplastic agents may induce anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

According to a further aspect of the invention there is provided a method of treatment or prophylaxis of chronic neurodegeneration, pain, migraine or cardiac hypertrophy, in a mammal in need thereof, which comprises administering to said mammal an effective amount of a compound of formula (I) or a pharmaceutically acceptable derivative thereof.

According to a further aspect of the invention there is provided the use of a compound of formula (I) or a pharmaceutically acceptable derivative thereof in the manufacture of a medicament for the prophylactic or therapeutic treatment of chronic neurodegeneration, pain, migraine or cardiac hypertrophy.

In order to use the compounds of formula (I) in therapy, they will normally be formulated into a pharmaceutical composition in accordance with standard pharmaceutical practice.

According to a further aspect of the invention there is provided a pharmaceutical composition comprising a compound of formula (I) or a pharmaceutically acceptable derivative thereof and a pharmaceutically acceptable carrier.

The compounds of formula (I) may conveniently be administered by any of the routes conventionally used for drug administration, for instance, parenterally, orally, topically or by inhalation. The compounds of formula (I) may be administered in conventional dosage forms prepared by combining it with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier is dictated by the amount of compound of formula (I) with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 g. When a liquid carrier is used, the preparation will be in the form of a syrup, emulsion, soft gelatin capsule, sterile injectable liquid such as an ampoule or nonaqueous liquid suspension.

The compounds of formula (I) are preferably administered parenterally, that is by intravenous, intramuscular, subcutaneous, sublingual, intranasal, intrarectal, intravaginal or intraperitoneal administration. The intravenous form of parenteral administration is generally preferred. The compounds may be administered as a bolus or continuous infusion e.g. for 6 hours up to 3 days. Appropriate dosage forms for such administration may be prepared by conventional techniques.

The compounds of formula (I) may also be administered orally. Appropriate dosage forms for such administration may be prepared by conventional techniques.

The compounds of formula (I) may also be administered by inhalation, that is by intranasal and oral inhalation administration. Appropriate dosage forms for such administration, such as aerosol formulations, may be prepared by conventional techniques.

The compounds of formula (I) may also be administered topically, that is by non-systemic administration. This includes the application of the inhibitors externally to the epidermis or the buccal cavity and the instillation of such a compound into the ear, eye and nose, such that the compound does not significantly enter the blood stream.

For all methods of use disclosed herein the daily oral dosage regimen will preferably be from about 0.1 to about 80 mg/kg of total body weight, preferably from about 0.2 to 30 mg/kg, more preferably from about 0.5 to 15 mg/kg. The daily parenteral dosage regimen about 0.1 to about 80 mg/kg of total body weight, preferably from about 0.2 to about 30 mg/kg, and more preferably from about 0.5 to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of the inhibitors will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the inhibitors given per day for a defined number of days, can be ascertained by those skilled in the art using conventional course of treatment determination tests. In the case of pharmaceutically acceptable salts the above figures are calculated as the parent compound of formula (I).

No toxicological effects are indicated/expected when a compound of formula (I) is administered in the above mentioned dosage range.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention and the following Descriptions illustrate the preparation of intermediates used in the preparation of these compounds.

Abbreviations used herein are as follows;

THF means tetrahydrofuran.

DMF means N,N-Dimethylformamide.

EXAMPLE 1

2-[5-(4-Chloro-3-hydroxy-phenyl)-4-pyridin yl-furan-2-yl]-2-methyl-propionitrile

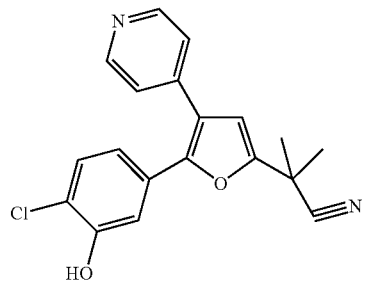

Step 1: 2,2-Dimethyl-3-oxo-5-pyridin-4-yl-pent-4-enenitrile

Pyridine-4-carboxaldehyde (6.9 ml, 72 mmol) was added to dry pyridine (16 ml) under argon. 2,2-Dimethyl-3-oxobutyronitrile {J. K. Rasmussen et al., *Synthesis*, 1973, 682} (8.0 g, 72 mmol) and diethylamine (7.3 ml, 71 mmol) were subsequently added and the solution heated under reflux for 18 hours. After cooling to room temperature, the mixture was poured into water and ethyl acetate. The mixture was separated and the aqueous phase re-extracted with ethyl acetate. The combined organic layers were dried and concentrated in vacuo to yield a solid which was triturated with diethyl ether to give the title compound (8.5 g, 59%); MS (ES+) m/e 201 [M+H]$^+$.

Step 2: 6-(4-Chloro-3-methoxy-phenyl)-2,2-dimethyl-3,6-dioxo-5-pyridin-4-yl-hexanenitrile A solution of the product of Example 1 Step 1 (4.0 g, 20.0 mmol) in DMF (7 ml) was added to a solution of sodium cyanide (300 mg, 6.12 mmol) in DMF (7 ml) over 15 minutes at room temperature. After stirring for a further 15 minutes, a solution of 4-chloro-3-methoxy-benzaldehyde (F. Claudi et al., *J. Med. Chem.*, 1992, 35, 4408) (640 mg, 3.75 mmol) in DMF (6 ml) was added dropwise. The mixture was stirred at room temperature for 18 hours and then diluted with water and the pH of the solution adjusted to 9 with aqueous sodium hydrogen carbonate solution. The mixture was extracted with chloroform and the organic phase washed with water and brine, dried and concentrated in vacuo. The residue was chromatographed on silica gel eluting with chloroform/ethanol/0.880 ammonia solution (90:9:1) to give the title compound (3.1 g, 42%); MS (ES+) m/e 371, 373 [M+H]$^+$.

Step 3: 2-[5-(4-Chloro-3-methoxy-phenyl)-4-pyridin-4-yl-furan-2-yl]-2-methyl-propionitrile (product A) and 2-[5-(4-chloro-3-methoxy-phenyl)-4-pyridin-4-yl-furan-2-yl]-isobutyramide (product B)

The product of Example 1 Step 2 (3.1 g, 8.4 mmol) was added to a stirred suspension of phosphorus pentoxide (35 g) in dry methane sulphonic acid (35 ml). After stirring at room temperature for 1 hour, the reaction mixture was cautiously poured into a stirred solution of saturated aqueous sodium hydrogen carbonate. The mixture was extracted with ethyl acetate and the organic phase washed with water and brine, dried and concentrated in vacuo. The residue was chromatographed on silica gel eluting with ethyl acetate to give product A (1.15 g, 39%); MS (ES+) m/e 353, 355 [M+H]$^+$.

Further elution of the column with ethyl acetate/methanol (9:1) yielded product B (0.83 g, 27% yield); MS (ES+) m/e 371, 373 [M+H]$^+$.

Step 4: 2-[5-(4-Chloro-3-hydroxy-phenyl)-4-pyridin-4-yl-furan-2-yl]-2-methyl-propionitrile A solution of product A from Example 1 Step 3 (100 mg, 0.28 mmol) in dichloromethane (10 ml) was cooled to 0° C. and treated with boron tribromide (1M solution in dichloromethane, 0.3 ml, 0.3 mmol). The mixture was stirred at 0° C. for 15 minutes and then at room temperature for 3 hours. The reaction was quenched by the addition of saturated aqueous sodium hydrogen carbonate solution, stirred for 15 minutes and then the product extracted into ethyl acetate (X 2). The organic phase was dried and concentrated in vacuo. The residue was chromatographed on silica gel eluting with chloroform/ethanol/0.880 ammonia solution (90:9:1) to give the title compound (70 mg, 73%); MS (ES+) m/e 339, 341 [M+H]$^+$.

EXAMPLE 2

2-[5-(4-Chloro-3-hydroxy-phenyl)-4-pyridin-4-yl-furan-2-yl]-isobutyramide

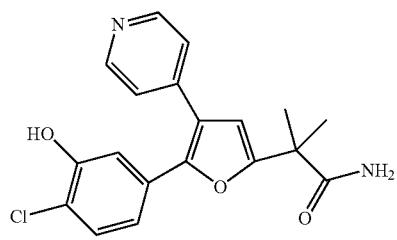

The title compound was prepared from product B from Example 1 Step 3 as described in Example 1 Step 4; MS (ES+) m/e 357, 359 [M+H]$^+$.

EXAMPLE 3

5-[5-(2-Amino-1,1-dimethyl-ethyl)-3-pyridin-4-yl-furan-2-yl]-2-chloro-phenol

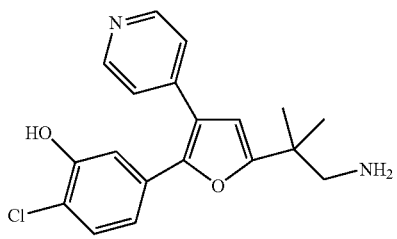

Step 1: 2-[5-(4-Chloro-3-methoxy-phenyl)-4-pyridin yl-furan-2-yl]-2-methyl-propylamine Borane-dimethylsulphide (1 ml, 10.5 mmol) was added to a solution of product A from Example 1 Step 3 (875 mg, 2.49 mmol) at room temperature. The mixture was heated to reflux for 2 hours, cooled, treated with methanol (3 ml) and then heated to reflux for a further 30 minutes. After concentrating in vacuo, the residue was dissolved in 2M hydrochloric acid (20 ml) and heated to reflux for 1 hour. The mixture was basified with aqueous sodium carbonate solution and the product extracted into chloroform (X 3), dried and concentrated in vacuo. The residue was chromatographed on silica gel eluting with chloroform/ethanol/0.880 ammonia solution (90:9:1) to give the title compound (620 mg, 70%); MS (ES+) m/e 357, 359 [M+H]$^+$.

Step 2: 5-[5-(2-Amino-1,1-dimethyl-ethyl)-3-pyridin-4-yl-furan-2-yl]-2-chloro-phenol The title compound was prepared from the product of Example 3 Step 1 as described in Example 1 Step 4; MS (ES+) m/e 343, 345 [M+H]$^+$.

EXAMPLE 4

1-(2-Methoxy-ethyl)-piperidinecarboxylic acid {2-[5-(4-chloro-3-hydroxy-phenyl)-4-pyridin-4-yl-furan-2-yl]-2-methyl-propyl}-amide

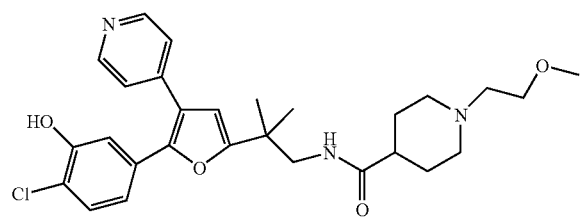

Step 1: 1-(2-Methoxy-ethyl)-piperidine-4-carboxylic acid ethyl ester

A solution of ethyl isonipecotate (26 g, 166 mmol) in ethanol (150 ml) was treated with potassium carbonate (41 g, 297 mmol) and 2-bromoethyl methyl ether (25 g, 179 mmol). After heating at reflux for 24 hours, the mixture was filtered and the solid washed with ethanol. The filtrate was concentrated in vacuo to yield the title compound (32.76 g, 92%); $^1$H NMR (CDCl$_3$) 4.12 (2H, q, J=7.1 Hz), 3.51 (2H, t, J=5.7 Hz), 3.33 (3H, s), 2.92 (2H, m), 2.56 (2H, t, J=5.7 Hz), 2.33-1.71 (7H, m) and 1.25 (3H, t, J7.1 Hz).

Step 2: 1-(2-Methoxy-ethyl)-piperidine-4-carboxylic acid hydrochloride

Concentrated hydrochloric acid (200 ml) was added to a suspension of the product of Example 4 Step 1 (20 g, 93 mmol) in water (120 ml). The mixture was heated at 100° C. for 60 hours, cooled to room temperature and the solvent concentrated in vacuo. The residue was azeotroped with toluene (×5) and dried over phosphorus pentoxide. The resulting solid was triturated with diethyl ether and acetone to yield the title compound (14.0 g, 81%); MS (ES−) m/e 186 [M−H]$^−$.

Step 3: 1-(2-Methoxy-ethyl)-piperidine-4-carboxylic acid {2-[5-(4-chloro-3-hydroxy-phenyl)-4-pyridin-4-yl-furan-2-yl]-2-methyl-propyl}-amide A solution of the product of Example 4 Step 2 (265 mg, 1.18 mmol) in DMF (5 ml) was treated with N-cyclohexylcarbodiimide, N'-methyl polystyrene (1.8 g) and 1-hydroxybenzotriazole hydrate (162 mg, 1.19 mmol). The mixture was stirred at room temperature for 30 minutes and then treated with a solution of the product of Example 3 Step 2 (407 mg, 1.19 mmol) in DMF (2 ml). After stirring for a further 16 hours, the reaction mixture was applied to a Bond Elut SCX cartridge. The cartridge was eluted with methanol and then 0.880 ammonia solution/methanol (1:9) to elute the product. After concentrating in vacuo, the product was purified further by chromatography on silica gel eluting with chloroform/ethanol/0.880 ammonia solution (90:9:1) to yield the title compound (340 mg, 56%); MS (ES+) m/e 512, 514 [M+H]$^+$.

EXAMPLE 5

2-[4-(4-Chloro-3-hydroxy-phenyl)-5-pyridin-4-yl-furan-2-yl]-2-methyl-propionitrile

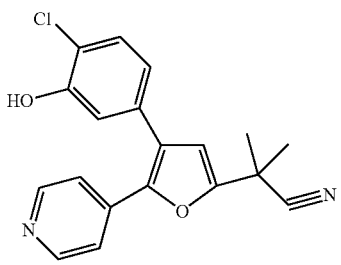

Step 1: 5-(4-Chloro-3-methoxy-phenyl)-2,2-dimethyl-3-oxo-pent-4-enenitrile

The title compound was prepared from 2,2-dimethyl-3-oxo-butyronitrile {J. K. Rasmussen et al., Synthesis, 1973, 682} and 4-chloro-3-methoxy-benzaldehyde (F. Claudi et al., J. Med. Chem., 1992, 35, 4408) as described in Example 1 Step 1; MS (ES−) m/e 263, 265 [M−H]$^−$.

Step 2. 5-(4-Chloro-3-methoxy-phenyl)-2,2-dimethyl-3,6-dioxo-6-pyridin-4-yl-hexanenitrile The title compound was prepared from the product of Example 5 Step 1 as described in Example 1 Step 2; MS (ES+) me 371, 373 [M+H]+.

Step 3: 2-[4-(4-Chloro-3-methoxy-phenyl)-5-pyridin-4-yl-furan-2-yl]-2-methyl-propionitrile (product A) and 2-[4-(4-chloro-3-methoxy-phenyl)-5-pyridin-4-yl-furan-2-yl]-isobutyramide (product B)

The title compounds were prepared from the product of Example 5 Step 2 as described in Example 1 Step 3 yielding product A (34% yield); MS (ES+) m/e 353, 355 [M+H]+ and product B (51% yield); MS (ES+) m/e 371, 373 [M+H]+.

Step 4: 2-[4-(4-Chloro-3-hydroxy-phenyl)-5-pyridin-4-yl-furan-2-yl]-2-methyl-propionitrile The title compound was prepared from product A from Example 5 Step 3 as described in Example 1 Step 4; MS (ES+) m/e 339, 341 [M+H]+.

EXAMPLE 6

2-[4-(4-Chloro-3-hydroxy-phenyl)-5-pyridin-4-yl-furan-2-yl]-isobutyramide

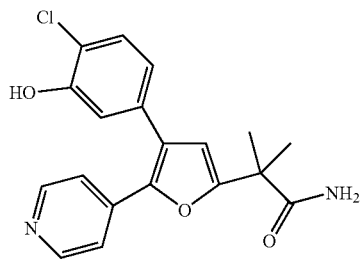

The title compound was prepared from product B from Example 5 Step 3 as described in Example 1 Step 4; MS (ES+) m/e 357, 359 [M+H]+.

EXAMPLE 7

2-[4-(4-Chloro-3-hydroxy-phenyl)-5-pyridin-4-yl-furan-2-yl]-2-methyl-propylamine

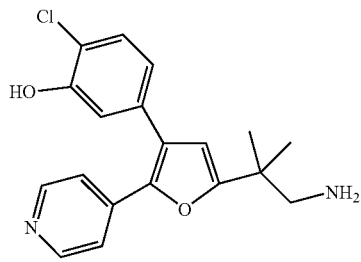

Step 1: 2-[4-(4-Chloro-3-methoxy-phenyl)-5-pyridin-4-yl-furan-2-yl]-2-methyl-propylamine The title compound was prepared from product A from Example 5 Step 3 as described in Example 3 Step 1; MS (ES+) m/e 357, 359 [M+H]+.

Step 2: 2-[4-(4-Chloro-3-hydroxy-phenyl)-5-pyridin-4-yl-furan-2-yl]-2-methyl-propylamine The title compound was prepared from the product of Example 7 Step 1 as described in Example 1 Step 4; MS (ES+) m/e 343, 345 [M+H]+.

EXAMPLE 8

1-(2-Methoxy-ethyl)-piperidine-4-carboxylic acid {2-[4-(4-chloro-3-hydroxy-phenyl)-5-pyridin-4-yl-furan-2-yl]-2-methyl-propyl}-amide

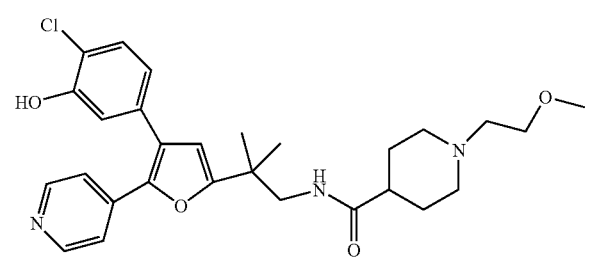

The title compound was prepared from the products of Example 7 Step 2 and Example 4 Step 2 using the method described in Example 4 Step 3; MS (ES+) m/e 512, 514 [M+H]+.

EXAMPLE 9

1-(2-Hydroxy-ethyl)-piperidine-4-carboxylic acid {2-[4-(4-chloro-3-hydroxy-phenyl)-5-pyridin-4-yl-furan-2-yl]-2-methyl-propyl}-amide

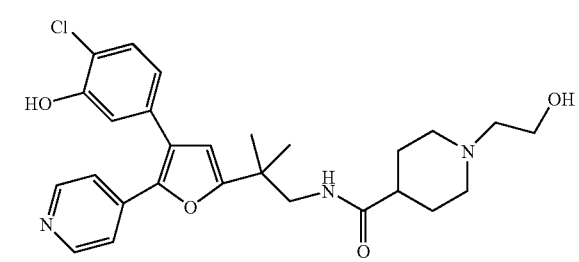

Step 1: 1-2-Hydroxy-ethyl)-piperidine-4-carboxylic acid {2-[4-(4-chloro-3-methoxy-phenyl)-5-pyridin-4-yl-furan-2-yl]-2-methyl-propyl}-amide The title compound was prepared from the products of Example 7 Step 1 and Example 4 Step 2 using the method described in Example 4 Step 3; MS (ES+) m/e 526, 528 [M+H]+.

Step 2: 1-(2-Hydroxy-ethyl)-piperidine-4-carboxylic acid {2-[4-(4-chloro-3-hydroxy-phenyl)-5-pyridin-4-yl-furan-2-yl]-2-methyl-propyl}-amide The title compound was prepared from the product of Example 9 Step 1 as described in Example 1 Step 4; MS (ES+) m/e 498, 500 [M+H]+.

EXAMPLE 10

N-{2-[4-(4-Chloro-3-hydroxy-phenyl)-5-pyridin-4-yl-furan-2-yl]-2-methyl-propyl}-2-morpholin-4-yl-acetamide

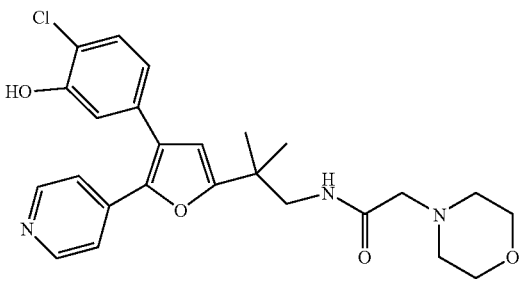

The title compound was prepared from the product of Example 7 Step 2 and morpholin-4-yl-acetic acid as described in Example 4 Step 3; MS (ES+) m/e 470, 472 [M+H]$^+$.

EXAMPLE 11

N-{2-[4-(4-Chloro-3-hydroxy-phenyl)-5-pyridin-4-yl-furan-2-yl]-2-methyl-propyl}-C-dimethylamino-acetamide

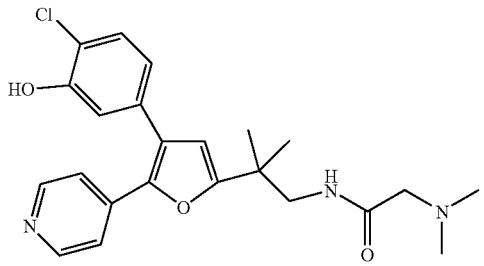

The title compound was prepared from the product of Example 7 Step 2 and dimethylamino-acetic acid hydrochloride as described in Example 4 Step 3; MS (ES+) m/e 428, 430 [M+H]$^+$.

EXAMPLE 12

Piperidine-4-carboxylic acid {2-[4-(4-chloro-3-hydroxy-phenyl)-5-pyridin-4-yl-furan-2-yl]-2-methyl-propyl}-amide

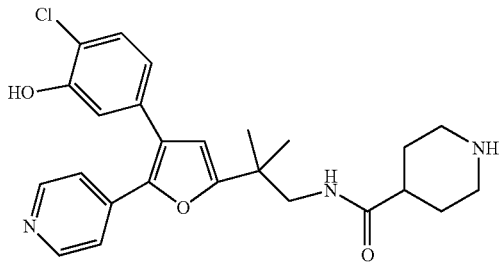

Step 1: 4-{2-[4-(4-Chloro-3-hydroxy-phenyl)-5-pyridin-4-yl-furan-2-yl]-2-methyl-propylcarbamoyl}-piperidine-1-carboxylic acid tert-butyl ester The title compound was prepared from the product of Example 7 Step 2 and N—BOC-isonipecotic acid as described in Example 4 Step 3; MS (ES+) m/e 554, 556 [M+H]$^+$.

Step 2: Piperidine-4-carboxylic acid {2-[4(4-chloro-3-hydroxy-phenyl)-5-pyridin-4-yl-furan-2-yl]-2-methyl-propyl}-amide A solution of the product of Example 12 Step 1 (110 mg, 0.19 mmol) in dichloromethane (5 ml) was treated with trifluoroacetic acid (1 ml). After stirring for 2 h, the mixture was concentrated, re-dissolved in dichloromethane and washed with saturated aqueous sodium hydrogen carbonate solution. The organic solution was dried and concentrated in vacuo to yield the title compound (80 mg, 93%); MS (ES+) m/e 454, 456 [M+H]$^+$.

It is to be understood that the present invention covers all combinations of particular and preferred subgroups described hereinabove.

BIOLOGICAL EXAMPLES

The activity of compounds of formula (I) as B-Raf inhibitors may be determined by the following in vitro assay:

Fluorescence Anisoptrophy Kinase Binding Assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10×Ki) of a potent inhibitor the anisotropy of the unbound fluorescent ligand is measurably different from the bound value.

The concentration of kinase enzyme should preferably be >1×$K_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

All compounds are serially diluted in DMSO, then by a one step dilution into buffer of comparison, 50 mM HEPES, pharmaceutical pH7.5, 1 mM CHAPS, 10 mM MgCL$_2$, for the assay.

B-Raf Enzyme concentration: 1 nM
Fluorescent ligand concentration: 0.5 nM
Test compound concentration: 0.5 nM-100 uM
Components incubated in 10 ul final volume in LJL HE 384 type B black microtitre plate until equilibrium reached (Over 3 h, up to 30 h)
Fluorescence anisotropy read in an LJL Acquest fluorescence reader.

Definitions: Ki=dissociation constant for inhibitor binding
Kf=dissociation constant for fluorescent ligand binding
The fluorescent ligand is the following compound:

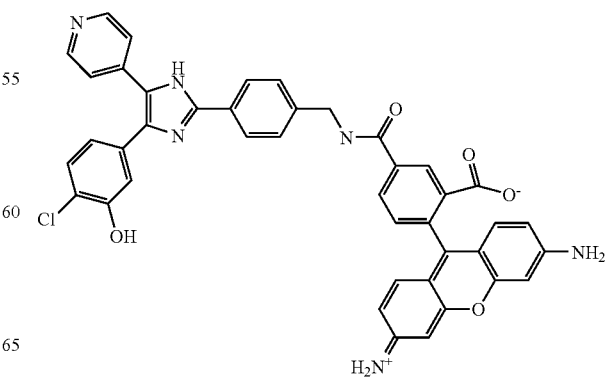

which is derived from 5-[2-(4-aminomethylphenyl)-5-pyridin-4-yl-1H-imidazol-4-yl]-2-chlorophenol and rhodamine green.

Compounds of the invention have a $K_d$ of less than 1 µM.

Raf Kinase Assay

Activity of human recombinant B-Raf protein was assessed in vitro by assay of the incorporation of radiolabelled phosphate to recombinant MAP kinase kinase(MEK), a known physiologic substrate of B-Raf. Catalytically active human recombinant B-Raf protein was obtained by purification from Sf9 insect cells infected with a human B-Raf recombinant baculovirus expression vector. To ensure that all substrate phosphorylation resulted from B-Raf activity, a catalytically inactive form of MEK was utilised. This protein was purified from bacterial cells expressing mutant inactive MEK as a fusion protein with glutathione-S-transferase (GST-kdMEK).

Method: Standard assay conditions of B-Raf catalytic activity utilised 3 ug of GST-kdMEK, 10 uM ATP and 2 uCi $^{33}$P-ATP, 50 mM MOPS, 0.1 mM EDTA, 0.1M sucrose, 10 mM $MgCl_2$ plus 0.1% dimethylsulphoxide (containing compound where appropriate) in a total reaction volume of 30 ul. Reactions were incubated at 25° C. for 90 minutes and reactions terminated by addition of EDTA to a final concentration of 50 uM. 10 ul of reaction was spotted to P81 phosphocellulose paper and air dried. Following four washes in ice cold 10% trichloroacetic acid, 0.5% phosphoric acid, papers were air dried prior to addition of liquid scintillant and measurement of radioactvity in a scintillation counter.

Results: The compounds of the examples were found to be effective in inhibiting B-Raf mediated phosphorylation of GST-kdMEK substrate having $IC_{50}$'s of <3 µM. The activity of compounds as Raf inhibitors may also be determined by the assays described in WO 99/10325; McDonald, O. B., Chen, W. J., Ellis, B., Hoffman, C., Overton, L., Rink, M., Smith, A., Marshall, C. J. and Wood, E. R. (1999) A scintillation proximity assay for the Raf/MEK/ERK kinase cascade: high throughput screening and identification of selective enzyme inhibitors, Anal. Biochem. 268: 318-329 and AACR meeting New Orleans 1998 Poster 3793.

The neuroprotective properties of B-Raf inhibitors may be determined by the following in vitro assay:

Neuroprotective Properties of B-Raf Inhibitors in Rat Hippocampal Slice Cultures Organotypic cultures provide an intermediate between dissociated neuronal cell cultures and in-vivo models of oxygen and glucose deprivation (OGD). The majority of glial-neuronal interactions and neuronal circuitry are maintained in cultured hippocampal slices, so facilitating investigation of the patterns of death among differing cell types in a model that resembles the in vivo situation. These cultures allow the study of delayed cellular damage and death 24 hours, or more, post-insult and permit assessment of the consequences of long-term alterations in culture conditions. A number of laboratories have reported delayed neuronal damage in response to OGD in organotypic cultures of the hippocampus (Vornov et al., Stroke, 1994, 25, 57465; Newell et al., Brain Res., 1995, 676, 3844). Several classes of compounds have been shown to protect in this model, including EAA antagonists (Strasser et al., Brain Res., 1995, 687, 167-174), Na channel blockers (Tasker et al., J. Neurosci., 1992, 12, 98-4308) and Ca channel blockers (Pringle et al., Stroke, 1996, 7, 2124-2130). To date, relatively little is known of the roles of intracellular kinase mediated signalling pathways in neuronal cell death in this model.

Method: Organotypic hippocampal slice cultures were prepared using the method of Stoppini et al., J. Neurosci. Methods, 1995, 37, 173-182. Briefly, 400 micron sections prepared from hippocampi of 7-8 day postnatal Sprague Dawley rats are cultured on semiporous membranes for 9-12 days. OGD is then induced by incubation in serum and glucose-free medium in an anaerobic chamber for 45 minutes. Cultures are then returned to the air/$CO_2$ incubator for 23 hours before analysis. Propidium iodide (PI) is used as an indicator of cell death. PI is non toxic to neurones and has been used in many studies to ascertain cell viability. In damaged neurons PI enters and binds to nucleic acids. Bound PI shows increased emission at 635 nm when excited at 540 nm. One PI fluorescence image and one white light image are taken and the proportion of cell death analysed. The area of region CA1 is defined from the white light image and superimposed over the PI image. The PI signal is thresholded and area of PI damage expressed as a percentage of the CA1 area. Correlation between PI fluorescence and histologically confirmed cell death has been validated previously by Niss1-staining using cresyl fast violet (Newell et al., J. Neurosci., 1995, 15, 7702-7711).

The anti-cancer properties of compounds of the invention may be determined by the following in vitro assays:

Methylene Blue Growth Inhibition Assay (Assay 2)

Normal human foreskin fibroblasts (HFF), human melanoma (A375P, SKMEL2, SKMEL3) colon carcinoma (Colo 205) were cultured in the following growth media: A375P, Colo 205, Roswell Park Memorial Institute (RPMI) 1640 (Life Technologies 22400-089) containing 10% fetal bovine serum (FBS); HFF, Dulbecco's modified Eagle Medium (DMEM) (Life Technologies 12320-032) containing 10% FBS; SKMEL2 and SKMEL3, Minimum Essential Medium (MEM, Life Technologies 11095-080) containing 1× non-essential amino acids (Life Technologies 11140-050) and 10% FBS. Cells were harvested using 0.25% trypsin/1 mM, EDTA, counted using a haemocytometer, and plated in 100 microliters of the appropriate media, at the following densities, in a 96-well tissue culture plate (Falcon 3075): HFF and A375P, 5,000 cells/well; all other cell lines, 10,000 cells/well. The next day, compounds were diluted in RPMI containing 100 micrograms/ml gentamicin, at twice the final required concentration, from 10 mM stock solutions in dimethyl sulphoxide (DMSO). One hundred microliters per well of these dilutions were added to the 100 microliters of media currently on the cell plates. RPMI containing 0.6% DMSO was added to control wells. Compounds diluted in. The final concentration of DMSO in all wells was 0.3%. Cells were incubated at 37° C., 5% $CO_2$ for 3 days. Medium was removed by aspiration. Cell biomass was estimated by staining cells with 90 µl per well methylene blue (Sigma M9140, 0.5% in 50:50 ethanol:water) and incubation at room temperature for at least 30 minutes. Stain was removed, the plates rinsed by immersion in deionized water and air-dried. To release stain from the cells 100 µl of solubilization solution was added (1% N-lauroyl sarcosine, sodium salt, Sigma L5125, in phosphate-buffered saline solution (PBS)), and plates were incubated at room temperature for 30 minutes. Optical density at 620 nM was measured on a microplate reader. Percent inhibition of cell growth was calculated relative to vehicle treated control wells. Concentration of compound that inhibits 50% of cell growth ($IC_{50}$) was interpolated using nonlinear regression (Levenberg-Marquardt) and the equation, $y=V_{max}*(1-(x/(K+x)))+Y2$, where "K" was equal to the $IC_{50}$.

XTT 72 Hr Growth Inhibition Protocol for Mammalian Cultured Cells (Assay 3)

Human diploid foreskin fibroblasts (HFF) or human colon carcinoma (Colo 201) cells were grown in Dulbecco's modified Eagle's medium (DMEM) (Invitrogen/Life Technologies) containing 10% fetal bovine serum (FBS) and the antibiotics penicillin (100 Units/ml) and streotomycin (100 micrograms/ml) (Invitrogen/Life Technologies). Growth was at 37° C. in humidified 5% CO2 incubators in 75 cm² plastic flasks. Cells were harvested using 0.25% trypsin/1 mM ethylenediaminetetraacetic acid (EDTA), resuspended in growth medium, and counted using a hemocytometer. Flat-bottomed 96-well plates were seeded with $2\times10^3$ cells/well in a volume of 200 ul from trypsinized exponentially growing cultures. To "blank" wells, growth medium was added with no additions. Cells were incubated overnight to permit attachment.

Next day, medium from wells that contained cells was replaced with 180 microliters of fresh medium. Appropriate dilutions of test compounds were added to the wells from stock solutions of compound dissolved in dimethyl sulfoxide (DMSO); final DMSO concentration in all wells was 0.2%. Cells plus compound were incubated for an additional 72 hr at 37° C. under normal growth conditions. Cells were then assayed for viability using standard XTT/PMS*. Fifty microliters of XTT/PMS solution was added to each well and plates were incubated for 90 minutes at 37° C. Absorbance at 450 nM was then determined using a 96-well UV plate reader (Molecular Devices). Under these conditions, absorbance of untreated control cells at 450 nm was at least 1.0 optical density unit/ml. Percent viability of cells in each well was calculated from these data (having been corrected for background absorbance). It was equal to $$100\times(\text{A450 test well/A450 untreated control well}),$$

the A450s being averages of triplicate determinations. IC50 was that concentration of compound that reduced cell viability to 50% of control (untreated) viability, as determined from plots of concentration vs percent viability.

*Preparation of XTT/PMS solution (immediately before assay).

For each 96-well plate, 8 mg XTT (2,3-bis[2-Methoxy-4-nitro-5-sulfophenyl]-2H-tetrazolium-5-carboxanilide) (Sigma Chemical Co.) per plate was dissolved in 100 ul DMSO. 3.9 ml $H_2O$ was added to dissolve XTT and 20 ul of PMS (phenazine methosulfate, Sigma Chemical Co.) stock solution (30 mg/ml) was added from frozen aliquoted stock solution (10 mg of PMS in 3.3 ml phosphate buffered saline (Invitrogen/Life Technologies). (These stocks are routinely frozen at −20° C. until use).

Normal human foreskin fibroblasts (HFF) are the control normal cell line that should not be inhibited or at least much less sensitive.

| | | Cell Line | HFF | Colo201 | Colo205 | A375P | SKMEL3 | SKMEL2 |
|---|---|---|---|---|---|---|---|---|
| | | Pathology | normal | Colorectal cancer | Colorectal cancer | melanoma | melanoma | melanoma |
| | | B-Raf Status | wt | ND | V599E | V599E | V599E | wt |
| | B-Raf, nM Kd | Ras Status | wt | ND | wt | wt | wt | [Q61R]N-Ras |
| Example No | Assay 1 | | | Assay 3 | Assay 3 | Assay 2 | Assay 2 | Assay 2 | Assay 2 |
| 3 | 5.5 | | | 22* | 8.5* | 7.9* | 1.8^Δ | 1.4^Δ | 4.9* |

*indicates IC50 >3 μM
^Δindicates IC50 0.3-3 μM
†indicates IC50 <0.3 μM
A375, Colo205 and SKMEL are reported as wild type (wt) for Ras status in the literature.
V599E indicates that the cell lines have activating BRaf mutation (V599E)
ND represents not determined Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of composition, process, or use claims and may include by way of example and without limitation the following claims.

The invention claimed is:
1. A compound of formula (II):

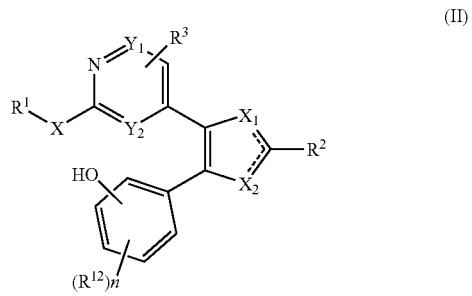

wherein:
X is O, $CH_2$, CO, S or NH, or the moiety X—$R^1$ is hydrogen;
$Y_1$ and $Y_2$ independently represent CH or N;
$R^1$ is hydrogen, $C_{1-6}$alkyl, $C_{3-7}$cycloalkyl, aryl, aryl $C_{1-6}$alkyl-, heterocyclyl, heterocyclyl$C_{1-6}$alkyl-, heteroaryl, or heteroaryl$C_{1-6}$alkyl-, any of which, except hydrogen, is optionally substituted;
$R^2$ is $C_{1-6}$ alkyl, $C_{3-7}$cycloalkyl, heterocyclyl, heterocyclyl$C_{1-6}$alkyl, hetero$C_{1-6}$alkyl, or $C_{1-6}$alkylhetero $C_{1-6}$alkyl, any one of which is may be optionally substituted;
Ar is a mono- or fused bicyclic aromatic or heteroaromatic group which is optionally substituted;

R³ is independently selected from hydrogen, halogen, $C_{1-6}$alkyl, aryl, aryl$C_{1-6}$alkyl, $C_{1-6}$alkoxy, $C_{1-6}$alkoxy$C_{1-6}$alkyl, halo$C_{1-6}$alkyl, aryl$C_{1-6}$alkoxy, hydroxy, nitro, cyano, azido, amino, mono- and di-N—$C_{1-6}$alkylamino, acylamino, arylcarbonylamino, acyloxy, carboxy, carboxy salts, carboxy esters, carbamoyl, mono- and di-N—$C_{1-6}$alkylcarbamoyl, $C_{1-6}$alkoxycarbonyl, aryloxycarbonyl, ureido, guanidino, $C_{1-6}$alkylguanidino, amidino, $C_{1-6}$alkylamidino, sulphonylamino, aminosulphonyl, $C_{1-6}$alkylthio, $C_{1-6}$alkylsulphinyl or $C_{1-6}$alkylsulphonyl; and one of $X_1$ and $X_2$ is selected from O or S and the other is CH, wherein $R^{11}$ is hydrogen, $C_{1-6}$alkyl, aryl or aryl$C_{1-6}$alkyl;

$R^{12}$ independently selected from halo, hydroxy, $C_{1-6}$alkyl, $C_{1-6}$alkoxy;

n is 0, 1 or 2;

or pharmaceutically acceptable salts thereof.

2. A compound, wherein the compound is:
2-[5-(4-Chloro-3-hydroxy-phenyl)-4-pyridin-4-yl-furan-2-yl]-2-methyl-propionitrile;
2-[5-(4-Chloro-3-hydroxy-phenyl)-4-pyridin-4-yl-furan-2-yl]-isobutyramide;
5-[5-(2-Amino-1,1-dimethyl-ethyl)-3-pyridin-4-yl-furan-2-yl]-2-chloro-phenol;
1-(2-Methoxy-ethyl)-piperidine-4-carboxylic acid {2-[5-(4-chloro-3-hydroxy-phenyl)-4-pyridin-4-yl-furan-2-yl]-2-methyl-propyl}-amide;
2-[4-(4-Chloro-3-hydroxy-phenyl)-5-pyridin-4-yl-furan-2-yl]-2-methyl-propionitrile;
2-[4-(4-Chloro-3-hydroxy-phenyl)-5-pyridin-4-yl-furan-2-yl]-isobutyramide;
2-[4-(4-Chloro-3-hydroxy-phenyl)-5-pyridin-4-yl-furan-2-yl]-2-methyl-propylamine;
1-(2-Methoxy-ethyl)-piperidine-4-carboxylic acid {2-[4-(4-chloro-3-hydroxy-phenyl)-5-pyridin-4-yl-furan-2-yl]-2-methyl-propyl}-amide;
1-(2-Hydroxy-ethyl)-piperidine-4-carboxylic acid {2-[4-(4-chloro-3-hydroxy-phenyl)-5-pyridin-4-yl-furan-2-yl]-2-methyl-propyl}-amide;
N-{2-[4-(4-Chloro-3-hydroxy-phenyl)-5-pyridin-4-yl-furan-2-yl]-2-methyl-propyl}-2-morpholin-4-yl-acetamide;
N-{2-[4-(4-Chloro-3-hydroxy-phenyl)-5-pyridin-4-yl-furan-2-yl]-2-methyl-propyl}-C-dimethylamino-acetamide; and
Piperidine-4-carboxylic acid {2-[4-(4-chloro-3-hydroxy-phenyl)-5-pyridin-4-yl-furan-2-yl]-2-methyl-propyl}-amide.

3. A pharmaceutical composition comprising a compound of formula (II) according to claim 1 or a pharmaceutically acceptable salt thereof and a pharmaceutically acceptable carrier.

4. A method for therapeutic treatment of colorectal cancer in a mammal, which comprises administering a therapeutically effective amount of a compound of formula (II) according to claim 1 or a pharmaceutically acceptable salt thereof.

5. The compound of formula (II) according to claim 1, wherein $R^2$ is an optionally substituted $C_{1-6}$alkyl group.

6. A method for therapeutic treatment of melanoma in a mammal, which comprises administering a therapeutically effective amount of a compound of formula (II) according to claim 1 or a pharmaceutically acceptable salt thereof.

* * * * *